(12) United States Patent
Tanaka et al.

(10) Patent No.: US 7,994,153 B2
(45) Date of Patent: Aug. 9, 2011

(54) CHLOASMA AMELIORATION COMPOSITION AND DULLNESS AMELIORATION COMPOSITION

(75) Inventors: Hideo Tanaka, Kyoto (JP); Masahiko Tanaka, Otsu (JP); Yasuo Furuta, Otsu (JP); Kosaburo Wakamatsu, Kyoto (JP); Junko Kamimura, Kyoto (JP); Fumiki Harano, Kyoto (JP); Mitsuaki Kawamura, Kyoto (JP); Shigekatsu Kawabata, Itano-gun (JP); Shigeo Shinohara, Kyoto (JP); Noboru Yoshino, Kyoto (JP)

(73) Assignee: Otsuka Pharmaceutical Co., Ltd., Tokyo (JP)

( * ) Notice: Subject to any disclaimer, the term of this patent is extended or adjusted under 35 U.S.C. 154(b) by 1708 days.

(21) Appl. No.: 10/514,833

(22) PCT Filed: May 19, 2003

(86) PCT No.: PCT/JP03/06175
§ 371 (c)(1),
(2), (4) Date: Nov. 18, 2004

(87) PCT Pub. No.: WO03/097072
PCT Pub. Date: Nov. 27, 2003

(65) Prior Publication Data
US 2005/0220827 A1 Oct. 6, 2005

(30) Foreign Application Priority Data

May 20, 2002 (JP) ................................ 2002-144735

(51) Int. Cl.
*A61K 8/02* (2006.01)
*A61K 31/7076* (2006.01)
*A61K 31/708* (2006.01)
*A61Q 19/00* (2006.01)

(52) U.S. Cl. .......................................... 514/47; 424/401
(58) Field of Classification Search .................. None
See application file for complete search history.

(56) References Cited

U.S. PATENT DOCUMENTS 4,279,262 A * 7/1981 Horin et al. ................... 132/202
4,294,852 A * 10/1981 Wildnauer et al. ............. 514/557
4,569,839 A * 2/1986 Grollier et al. .................. 424/74

(Continued)

FOREIGN PATENT DOCUMENTS

EP 1 498 101 A1 1/2005

(Continued)

OTHER PUBLICATIONS

Melasma. MedlinePlus Medical Dictionary. http://ww2.merriam-webster.com/cgi-bin/mwmednIm. Accessed Feb. 6, 2009.*

(Continued)

*Primary Examiner* — Andrew D Kosar
*Assistant Examiner* — Lori K Mattison
(74) *Attorney, Agent, or Firm* — Finnegan, Henderson, Farabow, Garrett & Dunner, L.L.P.

(57) ABSTRACT

The present invention provides a composition that can effectively improve melasma and a composition that can effectively reduce skin dullness.

The composition for improving melasma comprises a purine nucleic acid-related substance and a pharmaceutically or cosmetically acceptable carrier, and exhibits an excellent melasma improving effect due to the action of the purine nucleic acid-related substance contained. The composition for reducing skin dullness comprises a purine nucleic acid-related substance and a pharmaceutically or cosmetically acceptable carrier, and exhibits an excellent effect of reducing skin dullness due to the action of the purine nucleic acid-related substance contained.

8 Claims, 1 Drawing Sheet

U.S. PATENT DOCUMENTS

| | | | | |
|---|---|---|---|---|
| 4,946,832 | A | * | 8/1990 | Goode et al. .................. 514/53 |
| 5,160,739 | A | * | 11/1992 | Kanga ............................ 424/401 |
| 5,466,719 | A | * | 11/1995 | Jakobson et al. ............. 514/785 |
| 5,618,522 | A | * | 4/1997 | Kaleta et al. .................... 424/60 |
| 5,637,293 | A | * | 6/1997 | Honda ............................ 424/62 |
| 5,688,831 | A | * | 11/1997 | El-Nokaly et al. ........... 424/401 |
| 5,811,112 | A | * | 9/1998 | Chandar et al. ............... 424/401 |
| 5,932,608 | A | * | 8/1999 | Nguyen et al. ................ 514/415 |
| 5,955,109 | A | * | 9/1999 | Won et al. ..................... 424/501 |
| 6,060,041 | A | * | 5/2000 | Candau et al. ................. 424/59 |
| 6,074,652 | A | * | 6/2000 | Ishiwatari et al. ............ 424/401 |
| 6,316,012 | B1 | * | 11/2001 | N'Guyen et al. .............. 424/401 |
| 6,376,481 | B1 | * | 4/2002 | Bruce et al. .................... 514/169 |
| 6,465,440 | B2 | * | 10/2002 | von Borstel et al. ........... 514/45 |
| 6,946,436 | B2 | * | 9/2005 | Wakamatsu et al. .......... 510/417 |
| 2001/0007677 | A1 | * | 7/2001 | Nagatani et al. .............. 424/401 |
| 2001/0018568 | A1 | * | 8/2001 | Iga et al. ......................... 604/20 |
| 2001/0047039 | A1 | * | 11/2001 | McManus et al. ............. 516/98 |
| 2002/0006383 | A1 | * | 1/2002 | Anderson et al. ............. 424/401 |
| 2002/0006425 | A1 | * | 1/2002 | Takaoka et al. ............... 424/405 |
| 2002/0034525 | A1 | * | 3/2002 | Sakai et al. .................... 424/401 |
| 2004/0029761 | A1 | | 2/2004 | Wakamatsu et al. |
| 2004/0116373 | A1 | | 6/2004 | Okuda et al. |

FOREIGN PATENT DOCUMENTS

| | | | |
|---|---|---|---|
| JP | 47-26687 | B | 7/1972 |
| JP | 5-331142 | A | 12/1993 |
| JP | 7-277939 | A | 10/1995 |
| JP | 8-99860 | A | 4/1996 |
| JP | 8-119825 | A | 5/1996 |
| JP | 9-143063 | A | 6/1997 |
| JP | 9-183718 | A | 7/1997 |
| JP | 9-249550 | A | 9/1997 |
| JP | 9-291011 | A | 11/1997 |
| JP | 10-7541 | A | 1/1998 |
| JP | 10-95704 | A | 4/1998 |
| JP | 10-114670 | A | 5/1998 |
| JP | 10-182411 | A | 7/1998 |
| JP | 10-182412 | A | 7/1998 |
| JP | 11269049 | * | 10/1999 |
| JP | 2000-212025 | A | 8/2000 |
| JP | 2000-212056 | A | 8/2000 |
| JP | 2000-256188 | A | 9/2000 |
| JP | 2002-370986 | | 12/2002 |
| WO | WO 98/15276 | A1 | 4/1998 |
| WO | WO 99/55302 | | 11/1999 |
| WO | WO 00/24365 | | 5/2000 |
| WO | WO 02/41853 | A1 | 5/2002 |
| WO | WO 02/083087 | A1 | 10/2002 |

OTHER PUBLICATIONS

Mottled. Webster's Third New International Dictionary.*
Mottling. Stedman's 27$^{th}$ Edition. http://www.thomsonhc.com/pdrel/librarian/PFDefaultActionId/pdrcommon.Stedmans. Accessed Feb. 5, 2009.*
Karlshamns. International Magazine. Apr. 2002.*
Supplementary European Search Report dated Oct. 20, 2009, in Application No. 03728092.2.
Kitano Y., "Effects of dibutyryl adenosine 3',5'-cyclic monophosphate on human melanocytes in vitro," *Acta Dermatovener*, 56:223-28 (1976).
McGuire J., "Melanocyte function: Influence of cyclic adenosine monophosphate," *Clin. Pharmacol. and Therap.*, 16:954-58 (1974).
Piamphongsant T., "Treatment of melasma: a review with personal experience," *Inter. J. Dermatol.*, 37:897-903 (1998).
Wikswo M.A., "Action of cyclic AMP on pigment donation between mammalian melanocytes and keratinocytes," *Yale J. Biol. and Med.*, 46:592-601 (1973).

* cited by examiner

CHLOASMA AMELIORATION COMPOSITION AND DULLNESS AMELIORATION COMPOSITION

TECHNICAL FIELD

The present invention relates to a composition that can effectively improve melasma. The present invention also relates to a method for improving melasma. Further, the invention relates to a composition that can effectively reduce skin dullness. The invention also relates to a method for reducing skin dullness.

BACKGROUND OF THE INVENTION

Melasma is a disorder that occurs mainly in women, and produces light-brown symmetric areas of pigmentation on both sides of the face unaccompanied by inflammation. The cause of the disorder has not yet been fully elucidated, however melasma may develop primarily due to polyendrocrine abnormalities by estrogen, adrenal cortex hormone, ACTH, etc., in association with sunlight irradiation, pregnancy, dysfunction of the ovaries, the taking of oral contraceptives, the taking of antiepileptics, etc.

Conventionally, melasma is treated by methods for eliminating endogenous and exogenous causes of the disorder by (1) oral administration of vitamin C or a reduced glutathione agent, (2) elimination of causative agents such as drugs, etc., and (3) avoidance of sunlight irradiation by use of sunscreen (Hyojun Hifukagaku, 4th edition, pp 212-213, edited by Yoshio SATO, issued by Igaku-Shoin). However, the conventional treatment methods do not produce satisfactory effects and are thus unsatisfactory.

Skin dullness is a serious aesthetic problem particularly for women and specifically denotes skin conditions such as loss of skin clarity, skin muddiness due to body waste accumulation, and uneven skin color. Skin dullness may be caused by a combination of various factors, such as skin muddiness or skin shading due to a thickened horny cell layer accompanied by aging, reduced flushness in the skin, pigmentation, lowered skin resilience, yellowing of the skin, dirt such as sweat and sebum, etc.

As described above, since skin dullness is caused by the involvement of various factors, skin dullness cannot be effectively reduced even by substances that have been considered as useful for removing chloasma. Various substances useful for reducing skin dullness have been examined to date, however, at the present time, a substance that can satisfactorily reduce skin dullness has not developed.

It has been reported that purine nucleic acid-related substances exhibit various physiological functions, however it is not known that such substances can improve melasma and reduce skin dullness.

It is known that purine nucleic acid-related substances are hard to formulate. When the substance concerned is blended in a composition to be a concentration such that its effects can be exhibited, the prepared composition is inferior in feeling of use, stability, etc. In particular, the substance is very difficult to add it into an emulsion due to its property of reducing the strength of membranes formed at the oil-water interfaces. Therefore, in order to formulate the substance into an emulsion, such as a milky lotion or cream, it is necessary to develop a method for improve the stability of the emulsion.

DISCLOSURE OF THE INVENTION

An object of the present invention is to provide a composition that can effectively improve melasma, and a composition in the form of an O/W emulsion with favorable emulsification stability that can effectively improve melasma. Another object of the present invention is to provide a method for effectively improving melasma.

A further object of the invention is to provide a composition that can effectively reduce skin dullness, and a composition in the form of an O/W emulsion with favorable emulsification stability that can effectively reduce skin dullness. Another object of the present invention is to provide a method for effectively reducing skin dullness.

The present inventors carried out intensive research to solve the above-described problems, and found that purine nucleic acid-related substances present in the living body, in particular adenosine monophosphates, i.e., a monophosphoric acid ester of adenosine, or salts thereof are excellent at improving melasma and reducing skin dullness. Further, the inventors found that an excellent emulsification stability can be given to such purine nucleic acid-related substances, which hitherto have been difficult to emulsify without losing the effects thereof, by preparing an O/W emulsion by blending the above-mentioned purine nucleic acid-related substance with a polyglyceryl fatty acid ester, an alkanoyl lactic acid or salts thereof, an acrylic acid-alkyl methacrylate copolymer, water, and an oily component. The inventors conducted further research and accomplished the present invention based on these findings.

More specifically, the present invention relates to the following compositions for improving melasma:

Item 1. A composition for improving melasma comprising a purine nucleic acid-related substance and a pharmaceutically or cosmetically acceptable carrier.

Item 2. A composition for improving melasma according to Item 1, wherein the purine nucleic acid-related substance is an adenosine monophosphate or a salt thereof.

Item 3. A composition for improving melasma according to Item 1 or 2, comprising the purine nucleic acid-related substance in a proportion of at least 0.01 wt. % based on the total amount of the composition.

Item 4. A composition for improving melasma according to any one of Items 1 to 3, comprising the purine nucleic acid-related substance in a proportion of 1 to 10 wt. % based on the total amount of a composition.

Item 5. A composition for improving melasma according to any one of Items 1 to 4, wherein the composition has a pH in the range of 2 to 8.

Item 6. A composition for improving melasma according to any one of Items 1 to 5 used for an externally-applied medical or quasi-medical drug, or a cosmetic.

Item 7. A composition for improving melasma according to any one of Items 1 to 6, wherein the composition further comprises a polyglyceryl fatty acid ester, an alkanoyl lactic acid or a salt thereof, an acrylic acid-alkyl methacrylate copolymer, water, and an oil, and is formulated into an O/W-type emulsification.

Item 8. A composition for improving melasma according to Item 7, further comprising a polyhydric alcohol.

Item 9. A composition for improving melasma according to Item 7 or 8, wherein the polyglyceryl fatty acid ester is an ester of a $C_{12-36}$ fatty acid and a polyglycerol having a polymerization degree of 6 or more.

Item 10. A composition for improving melasma according to any one of Items 7 to 9, wherein the alkanoyl lactic acid comprises an alkanoyl group having 8 or more carbons.

Item 11. A composition for improving melasma according to any one of Items 7 to 10, wherein the acrylic acid-alkyl methacrylate copolymer comprises a $C_{5-40}$ alkyl group.

Item 12. A composition for improving melasma according to any one of Items 7 to 11, wherein the oil is a hydrocarbon liquid oil.

Item 13. A composition for improving melasma according to any one of Items 7 to 12, wherein the polyglyceryl fatty acid ester is an ester of a $C_{12-36}$ fatty acid and a polyglycerol having a polymerization degree of 6 or more, the alkanoyl alkanoyl lactic acid comprises an alkanoyl group having 8 or more carbons, the acrylic acid-alkyl methacrylate copolymer comprises a $C_{5-40}$ alkyl group, and the oil is a hydrocarbon liquid oil.

Item 14. A composition for improving melasma according to Item 8, wherein the polyglyceryl fatty acid ester is included in a proportion of 0.05 to 6 wt. %, the alkanoyl alkanoyl lactic acid or a salt thereof is included in a proportion of 0.01 to 1 wt. %, the acrylic acid-alkyl methacrylate copolymer is included in a proportion of 0.01 to 0.8 wt. %, the oil is included in a proportion of 0.3 to 20 wt. %, the polyhydric alcohol is included in a proportion of 0.05 to 15 wt. %, and water is included in a proportion of 50 to 90 wt. %, based on the total amount of the composition.

Item 15. A composition for improving melasma according to any one of Items 7 to 14, wherein the polyglyceryl fatty acid ester and the alkanoyl alkanoyl lactic acid or a salt thereof are included in a weight ratio of 95:5 to 60:40.

Item 16. A composition for improving melasma according to any one of Items 7 to 15, further comprising a lower alcohol.

The present invention also relates to the following compositions for reducing skin dullness:

Item 17. A composition for reducing skin dullness comprising a purine nucleic acid-related substance, and a pharmaceutically or cosmetically acceptable carrier.

Item 18. A composition for reducing skin dullness according to Item 17, wherein the purine nucleic acid-related substance is an adenosine monophosphate or a salt thereof.

Item 19. A composition for reducing skin dullness according to Item 17 or 18, comprising the purine nucleic acid-related substance in a proportion of at least 0.01 wt. % based on the total amount of the composition.

Item 20. A composition for reducing skin dullness according to any one of Items 17 to 19, comprising the purine nucleic acid-related substance in a proportion of 1 to 10 wt. % based on the total amount of the composition.

Item 21. A composition for reducing skin dullness according to any one of Items 17 to 20, wherein the composition has a pH in the range of 2 to 8.

Item 22. A composition for reducing skin dullness according to any one of Items 17 to 21 used for an externally-applied medical or quasi-medical drug, or a cosmetic.

Item 23. A composition for reducing skin dullness according to any one of Items 17 to 22, wherein the composition further comprises a polyglyceryl fatty acid ester, an alkanoyl alkanoyl lactic acid or a salt thereof, an acrylic acid-alkyl methacrylate copolymer, water, and an oil, and is formulated into an O/W-type emulsification.

Item 24. A composition for reducing skin dullness according to Item 23, further comprising a polyhydric alcohol.

Item 25. A composition for reducing skin dullness according to Item 23 or 24, wherein the polyglyceryl fatty acid ester is an ester of a $C_{12-36}$ fatty acid and a polyglycerol having a polymerization degree of 6 or more.

Item 26. A composition for reducing skin dullness according to any one of Items 23 to 25, wherein the alkanoyl alkanoyl lactic acid comprises an alkanoyl group having 8 or more carbons.

Item 27. A composition for reducing skin dullness according to any one of Items 23 to 26, wherein the acrylic acid-alkyl methacrylate copolymer comprises a $C_{5-40}$ alkyl group.

Item 28. A composition for reducing skin dullness according to any one of Items 23 to 27, wherein the oil is a hydrocarbon liquid oil.

Item 29. A composition for reducing skin dullness according to Item 23, wherein the polyglyceryl fatty acid ester is an ester of a $C_{12-36}$ fatty acid and a polyglycerol having a polymerization degree of 6 or more, the alkanoyl alkanoyl lactic acid comprises an alkanoyl group having 8 or more carbons, the acrylic acid-alkyl methacrylate copolymer comprises a $C_{5-40}$ alkyl group, and the oil is a hydrocarbon liquid oil.

Item 30. A composition for reducing skin dullness according to Item 24, wherein the polyglyceryl fatty acid ester is included in a proportion of 0.05 to 6 wt. %, the alkanoyl alkanoyl lactic acid or a salt thereof is included in a proportion of 0.01 to 1 wt. %, the acrylic acid-alkyl methacrylate copolymer is included in a proportion of 0.01 to 0.8 wt. %, the oil is included in a proportion of 0.3 to 20 wt. %, the polyhydric alcohol is included in a proportion of 0.05 to 15 wt. %, and water is included in a proportion of 50 to 90 wt. %, based on the total amount of the composition.

Item 31. A composition for reducing skin dullness according to any one of Items 23 to 30, wherein the polyglyceryl fatty acid ester and the alkanoyl alkanoyl lactic acid or a salt thereof are included in a weight ratio of 95:5 to 60:40.

Item 32. A composition for reducing skin dullness according to any one of Items 23 to 31, further comprising a lower alcohol.

The present invention further relates to the following methods for improving melasma:

Item 33. A method for improving melasma, comprising applying a purine nucleic acid-related substance to a melasma lesion.

Item 34. A method for improving melasma according to Item 33, wherein the purine nucleic acid-related substance is an adenosine monophosphate or a salt thereof.

Item 35. A method for improving melasma according to Item 33 or 34, comprising applying a composition comprising the purine nucleic acid-related substance in a proportion of at least 0.01 wt. % based on the total amount of the composition to the melasma lesion.

Item 36. A method for improving melasma according to Item 33 or 34, comprising applying a composition comprising the purine nucleic acid-related substance in a proportion of 1 to 10 wt. % based on the total amount of the composition to the melasma lesion.

Item 37. A method for improving melasma according to Item 35 or 36, wherein the composition has a pH in the range of 2 to 8.

Item 38. A method for improving melasma according to any one of Items 35 to 37, wherein the composition is used for an externally-applied medical or quasi-medical drug, or a cosmetic.

Item 39. A method for improving melasma according to any one of Items 35 to 38, wherein the composition further comprises a polyglyceryl fatty acid ester, an alkanoyl lactic acid or a salt thereof, an acrylic acid-alkyl methacrylate copolymer, water, and an oil, and is formulated into an O/W-type emulsification.

Item 40. A method for improving melasma according to Item 39, wherein the composition further comprises a polyhydric alcohol.

Item 41. A method for improving melasma according to Item 39 or 40, wherein the polyglyceryl fatty acid ester is an ester of a $C_{12-36}$ fatty acid and a polyglycerol having a polymerization degree of 6 or more.

Item 42. A method for improving melasma according to any one of Items 39 to 41, wherein the alkanoyl lactic acid comprises an alkanoyl group having 8 or more carbons.

Item 43. A method for improving melasma according to any one of Items 39 to 42, wherein the acrylic acid-alkyl methacrylate copolymer comprises a $C_{5-40}$ alkyl group.

Item 44. A method for improving melasma according to any one of Items 39 to 43, wherein the oil is a hydrocarbon liquid oil.

Item 45. A method for improving melasma according to Item 39, wherein the polyglyceryl fatty acid ester is an ester of a $C_{12-36}$ fatty acid and a polyglycerol having a polymerization degree of 6 or more, the alkanoyl lactic acid comprises an alkanoyl group having 8 or more carbons, the acrylic acid-alkyl methacrylate copolymer comprises a $C_{5-40}$ alkyl group, and the oil is a hydrocarbon liquid oil.

Item 46. A method for improving melasma according to Item 40, wherein the composition comprises the polyglyceryl fatty acid ester in a proportion of 0.05 to 6 wt. %, the alkanoyl lactic acid or a salt thereof in a proportion of 0.01 to 1 wt. %, the acrylic acid-alkyl methacrylate copolymer in a proportion of 0.01 to 0.8 wt. %, the oil in a proportion of 0.3 to 20 wt. %, the polyhydric alcohol in a proportion of 0.05 to 15 wt. %, and water in a proportion of 50 to 90 wt. %, based on the total amount of the composition.

Item 47. A method for improving melasma according to any one of Items 39 to 46, wherein the composition comprises the polyglyceryl fatty acid ester and the alkanoyl lactic acid or a salt thereof in a weight ratio of 95:5 to 60:40.

Item 48. A method for improving melasma according to any one of Items 39 to 47, wherein the composition further comprises a lower alcohol.

The present invention further relates to the following methods for reducing skin dullness:

Item 49. A method for reducing skin dullness, comprising applying a purine nucleic acid-related substance to a dullness region of the skin.

Item 50. A method for reducing skin dullness according to Item 49, wherein the purine nucleic acid-related substance is an adenosine monophosphate or a salt thereof.

Item 51. A method for reducing skin dullness according to Item 49 or 50, comprising applying a composition comprising the purine nucleic acid-related substance in a proportion of at least 0.01 wt. % based on the total amount of the composition to the dullness region of the skin.

Item 52. A method for reducing skin dullness according to Item 49 or 50, comprising applying a composition comprising the purine nucleic acid-related substance in a proportion of 1 to 10 wt. % based on the total amount of the composition to the dullness region of the skin.

Item 53. A method for reducing skin dullness according to Item 51 or 52, wherein the composition has a pH in the range of 2 to 8.

Item 54. A method for reducing skin dullness according to any one of Items 51 to 53, wherein the composition is used for an externally-applied medical or quasi-medical drug, or a cosmetic.

Item 55. A method for reducing skin dullness according to any one of Items 51 to 54, wherein the composition further comprises a polyglyceryl fatty acid ester, an alkanoyl lactic acid or a salt thereof, an acrylic acid-alkyl methacrylate copolymer, water, and an oil, and is formulated into an O/W-type emulsification.

Item 56. A method for reducing skin dullness according to Item 55, wherein the composition further comprises a polyhydric alcohol.

Item 57. A method for reducing skin dullness according to Item 55 or 56, wherein the polyglyceryl fatty acid ester is an ester of a $C_{12-36}$ fatty acid and a polyglycerol having a polymerization degree of 6 or more.

Item 58. A method for reducing skin dullness according to any one of Items 55 to 57, wherein the alkanoyl lactic acid comprises an alkanoyl group having 8 or more carbons.

Item 59. A method for reducing skin dullness according to any one of Items 55 to 58, wherein the acrylic acid-alkyl methacrylate copolymer comprises a $C_{5-40}$ alkyl group.

Item 60. A method for reducing skin dullness according to any one of Items 55 to 59, wherein the oil is a hydrocarbon liquid oil.

Item 61. A method for reducing skin dullness according to any one of Items 55 to 60, wherein the polyglyceryl fatty acid ester is an ester of a $C_{12-36}$ fatty acid and a polyglycerol having a polymerization degree of 6 or more, the alkanoyl lactic acid comprises an alkanoyl group having 8 or more carbons, the acrylic acid-alkyl methacrylate copolymer comprises a $C_{5-40}$ alkyl group, and the oil is a hydrocarbon liquid oil.

Item 62. A method for reducing skin dullness according to Item 56, wherein the composition comprises the polyglyceryl fatty acid ester in a proportion of 0.05 to 6 wt. %, the alkanoyl lactic acid or a salt thereof in a proportion of 0.01 to 1 wt. %, the acrylic acid-alkyl methacrylate copolymer in a proportion of 0.01 to 0.8 wt. %, the oil in a proportion of 0.3 to 20 wt. %, the polyhydric alcohol in a proportion of 0.05 to 15 wt. %, and water in a proportion of 50 to 90 wt. %, based on the total amount of the composition.

Item 63. A method for reducing skin dullness according to any one of Items 55 to 62, wherein the composition comprises the polyglyceryl fatty acid ester and the alkanoyl lactic acid or a salt thereof in a weight ratio of 95:5 to 60:40.

Item 64. A method for reducing skin dullness according to any one of Items 55 to 63, wherein the composition further comprises a lower alcohol.

The present invention also relates to the following modes of embodiment:

Item 65. Use of a purine nucleic acid-related substance for preparing a composition for improving melasma.

Item 66. Use of a purine nucleic acid-related substance for reducing skin dullness.

Item 67. Use of a purine nucleic acid-related substance for improving melasma.

Item 68. Use of a purine nucleic acid-related substance for reducing skin dullness.

Figure 1:
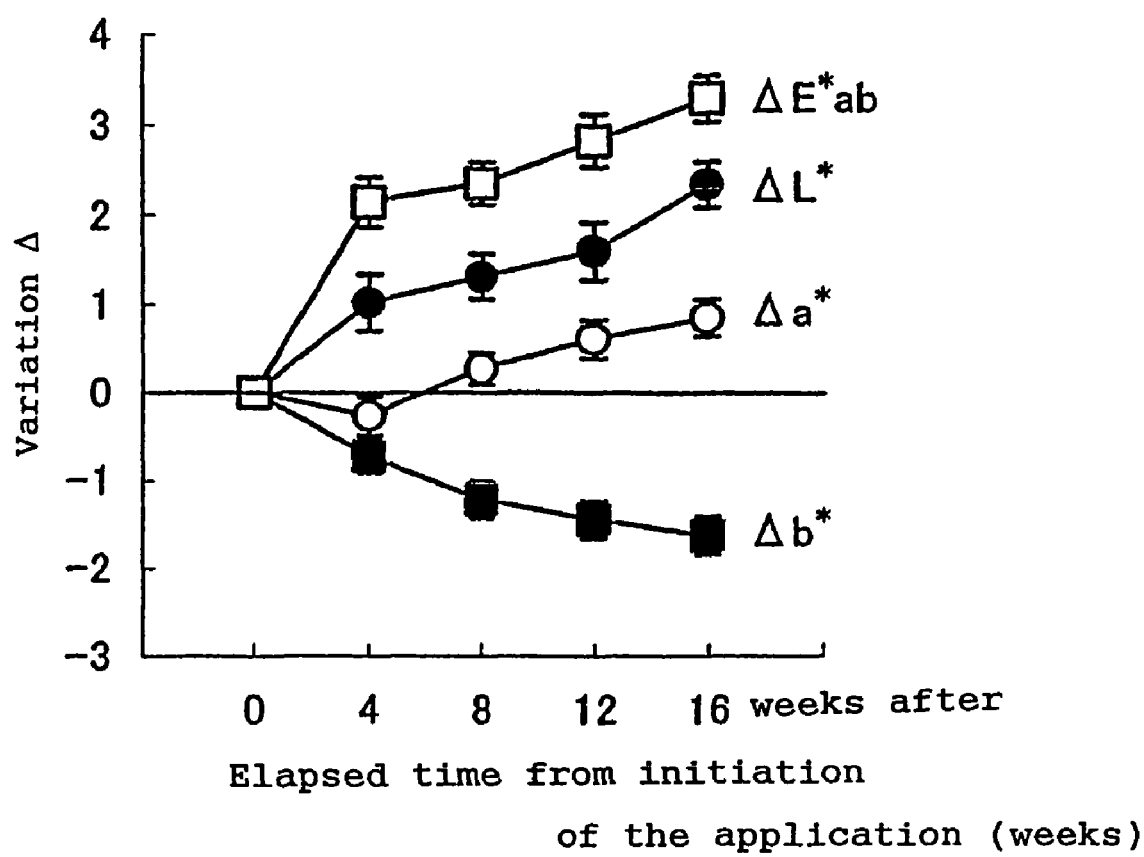
FIG. 1 shows the mean average of the variation, $\Delta L^*$ of an $L^*$ value indicating skin lightness of the skin, the mean average of the variation, $\Delta a^*$ of an $a^*$ value indicating redness of the skin, the variation, $\Delta b^*$ of an $b^*$ value indicating yellowness of the skin, and the variation, $\Delta E^*ab$ of color difference of the skin, $E^*ab$, 4, 8, 12, and 16 weeks after initiation of the application of the composition as compared to the $L^*$ value, the $a^*$ value and the $b^*$ value of the skin of the subjects before initiation of the application of the composition.

BEST MODE FOR CARRYING OUT THE INVENTION (1) A Composition for Improving Melasma The composition for improving melasma of the present invention comprises a purine nucleic acid-related substance and a pharmaceutically or cosmetically acceptable carrier.

The purine nucleic acid-related substances used in the invention, which may be hereinafter referred to as a purine base, denotes a purine or various purine derivatives having a purine nucleus as a skeleton, and salts thereof. Purine nucleic acid-related substances usable in the invention are not restricted insofar as the effect of improving melasma is exhibited when applied to the skin. Any purine nucleic acid-related substances that can be incorporated into cosmetics, externally-applied medical and quasi-medical drugs may be used without limitation. Those that are water soluble or hydrophilic are preferable. Examples of purine bases include adenine, guanine, hypoxanthine, xanthine, adenosine, guanosine, inosine, adenosine phosphates [adenosine 2'-monophosphate, adenosine 3'-monophosphate, adenosine 5'-monophosphate (AMP), cyclic adenosine 3'5'-monophosphate (cAMP), adenosine 5'-diphosphate (ADP), adenosine 5'-triphosphate (ATP)], guanosine phosphates (guanosine 3'-monophosphate, guanosine 5'-monophosphate, guanosine 5'-diphosphate, guanosine 5'-triphosphate), adenylosuccinic acid, xanthylic acid, inosinic acid, flavine adenine dinucleotide (FAD), nicotinamide adenine dinucleotide (NAD) and the like. Preferable among these are adenine, guanine, adenosine monophosphates (adenosine 2'-monophosphate, adenosine 3'-monophosphate, AMP, and cAMP), ADP, ATP, FAD and NAD. Preferable among the above are adenosine monophosphates, and particularly preferably AMP.

In the invention, purine base salts can be used in place of or in combination with purine bases. Examples of such purine base salts include alkali metal salts such as sodium salts and potassium salts; alkaline earth metal salts such as calcium salts, magnesium salts, and barium salts; salts of basic amino acids such as arginine and lysine; salts of ammoniums such as ammonium, tricyclohexylammonium salts; and salts of alkanolamines such as monoethanolamine, diethanolamine, triethanolamine, monoisopropanolamine, diisopropanolamine and triisopropanolamine. Alkali metal salts of purine bases are preferable. Monosodium adenosine monophosphate and disodium adenosine monophosphate are particularly preferable.

Purine nucleic acid-related substances can be used singly or in combination of two species or more. The manner of combination is not particularly restricted insofar as it does not impair the effects of the invention.

Any pharmaceutically or cosmetically acceptable carriers can be used without limitation for the composition for improving melasma of the invention. Examples of such carriers include water, oils, etc. Specific examples of such water types and oils are the same as the substances for preparing an emulsion composition described later. Such pharmaceutically or cosmetically acceptable carriers may be used singly or in combination.

The proportion of purine nucleic acid-related substances incorporated into the composition for improving melasma of the invention can be determined according to the form, the target, the desired effects or the like of the composition. More specifically, 0.01 wt. % can be mentioned as a lower limit of the proportion for incorporating the purine nucleic acid-related substances, based on the total amount of the composition for improving melasma. The upper limit thereof is not limited in view of the effects of the invention, and may be within the range that is acceptable for preparing the composition. For instance, 10 wt. % can be mentioned as an upper limit of the proportion for incorporating the purine nucleic acid-related substances based on the total amount of the composition. Preferable examples of the proportion for incorporating the purine nucleic acid-related substances include 0.01 to 10 wt. %, more preferably 1 to 10 wt. %, and especially preferably 3 to 6 wt. %, based on the total amount of the composition. The effect of improving melasma tends to be reduced when the proportion is much lower than 0.01 wt. %.

The composition for improving melasma of the invention may contain, as required, a wide variety of additives typically incorporated into externally-applied preparations, such as externally-applied medical or quasi-medical drugs, or cosmetics. Examples of such additives include surfactants, solubilizing components, emulsifiers, colorants (dyes, pigments), aromatic substances, antiseptics, bactericides, thickeners, antioxidants, sequestrants, pH adjusters, and deodorizers. Such components can be used singly or in combination of two species or more.

The composition for improving melasma of the invention may further contain various medicinal agents such as humectants, UV absorbers, whiteners, UV dispersants, vitamins, plant extracts, astringents, anti-inflammatory agents, cell activators, etc. Such components can be used singly or in combination of two species or more.

The composition for improving melasma of the invention can be made into various desired forms such as liquids, an oil, lotions, liniments, emulsions, suspensions, creams, ointments, sheets, aerosols, sprays, sticks and the like.

In particular, the composition for improving melasma of the invention is preferably formulated into emulsion compositions such as emulsions, creams, etc. in the form of an O/W emulsion composition as described below. In the O/W emulsion composition, the composition for improving melasma of the invention can be formulated into a stable emulsion form without separation, oil floating, etc., and in addition, the purine nucleic acid-related substance can effectively improve melasma.

The O/W emulsion composition can be prepared by blending and emulsifying a polyglyceryl fatty acid ester, an alkanoyl lactic acid or a salt thereof, an acrylic acid-alkyl methacrylate copolymer, water, and an oil with the above-mentioned purine nucleic acid-related substance.

Polyglyceryl fatty acid esters usable in the present invention are not limited. Examples include esters of a $C_{12-36}$ fatty acid and a polyglycerol having a polymerization degree of 6 or more, especially 6 to 10. Fatty acids that form esters with polyglycerols include saturated, unsaturated, linear and branched fatty acids. Specific examples are capric acid, lauric acid, isotridecanoic acid, myristic acid, palmitic acid, palmitoleic acid, stearic acid, isostearic acid, oleic acid, linoleic acid, behenic acid, ricinolic acid, and the like.

Specific examples of polyglyceryl fatty acid esters are hexaglycerol monolaurate, hexaglycerol monoisostearate, hexaglycerol monomyristate, hexaglycerol dioleate, hexaglycerol dimyristate, hexaglycerol dipalmitate, hexaglycerol distearate, hexaglycerol dibehenylate, hexaglycerol trilaurate, hexaglycerol trimyristate, hexaglycerol tripalmitate, hexaglycerol tristearate, hexaglycerol tribehenylate, hexaglycerol tetralaurate, hexaglycerol tetramyristate, hexaglycerol tetrapalmitate, hexaglycerol tetrastearate, hexaglycerol tetrabehenylate, hexaglycerol pentalaurate, hexaglycerol pentamyristate, hexaglycerol pentapalmitate, hexaglycerol pentastearate, hexaglycerol pentabehenylate, decaglyceryl monocaprate, decaglyceryl monolaurate, decaglyceryl monomyristate, decaglyceryl monopalmitate, decaglyceryl monostearate, decaglyceryl monooleate, decaglyceryl monolinoleate, decaglyceryl monoisostearate, decaglyceryl dicaprate, decaglyceryl dilaurate, decaglyceryl dimyristate, decaglyceryl dipalmitate, decaglyceryl distearate, decaglyceryl diisostearate, decaglyceryl trilaurate, decaglyceryl trimyristate, decaglyceryl tripalmitate, decaglyceryl tristearate, decaglyceryl trioleate, decaglyceryl tribehenylate, decaglyceryl pentastearate, decaglyceryl pentaoleate, decaglyceryl pentaisostearate, decaglyceryl heptastearate, decaglyceryl decastearate, decaglyceryl decaoleate, decaglyceryl decaisostearate, and the like. However, the polyglyceryl fatty acid esters are not limited thereto.

Such polyglyceryl fatty acid esters may be used singly or in combination. Polyglyceryl fatty acid esters having an HLB value of 10 or more, especially 10 to 15, can be suitably used. It is preferable to use the polyglyceryl fatty acid ester in a proportion of 0.05 to 6 wt. % based on the total amount of the composition for improving melasma, more preferably in a proportion of 0.1 to 5.5 wt. %.

Alkanoyl lactic acids usable in the invention are not limited. Examples include alkanoyl lactic acids having an alkanoyl group with 8 or more carbons, preferably alkanoyl lactic acids having a $C_{8-18}$ alkanoyl group. Specific examples include octanoyl lactic acid, caproyl lactic acid, 2-ethyl hexanoyl lactic acid, lauroyl lactic acid, myristoyl lactic acid, palmitoyl lactic acid, stearoyl lactic acid, isostearoyl lactic acid, oleoyl lactic acid, 12-hydroxystearoyl lactic acid, linoleyl lactic acid, and behenoyl lactic acid. Preferable are stearoyl lactic acid and isostearoyl lactic acid. Such alkanoyl lactic acids can be used in the form of salts. Examples of such salts include sodium salts, potassium salts, and like alkali metal salts; ammonium salts, triethanolamine salts, and the like. Preferred are sodium salts, more specifically, sodium stearoyl lactate and sodium isostearoyl lactate. Such alkanoyl lactic acids and salts thereof may be used singly or in combination. It is preferable to use the alkanoyl lactic acid or a salt thereof in a proportion of 0.01 to 1 wt. % based on the total amount of the composition for improving melasma, more preferably in a proportion of 0.1 to 0.5 wt. %.

The proportion for blending the polyglyceryl fatty acid ester with the alkanoyl lactic acid or a salt thereof is desirably such that the HLB value of the mixture be 10 or more, preferably 10 to 13. Specific examples of the proportion for blending the polyglyceryl fatty acid ester with the alkanoyl lactic acid or a salt thereof are weight ratios of 95:5 to 60:40, preferably 90:10 to 70:30.

Acrylic acid-alkyl methacrylate copolymers usable in the invention are not limited. Typical examples usually include those having an alkyl chain with 5 to 40 carbons. Preferred are those having an alkyl chain with 10 to 30 carbons. Although not limited thereto, such polymers are commercially available, for example, from Noveon Inc. under the trademarks of Carbopol and Pemulen, such as Carbopol 1342, Pemulen TR-1, and Pemulen TR-2. Such acrylic acid-alkyl methacrylate copolymers may be used singly or in combination. It is preferable to use the acrylic acid-alkylmethacrylate copolymer in a proportion of 0.01 to 0.8 wt. % based on the total amount of the composition for improving melasma, more preferably in a proportion of 0.3 to 0.6 wt. %, still more preferably in a proportion of 0.4 to 0.6 wt. %.

Any types of water can be used without limitation insofar as they are pharmaceutically or cosmetically acceptable. For instance, distilled water, ion-exchanged water, sterilized water, or electrolyte-containing water can be used as the water ingredient. Examples of electrolyte-containing water include sea water, hot-spring water, mineral water, and the like. The term "sea water" herein refers to surface sea water, intermediate sea water, deep sea water, and ultra deep sea water. The proportion of the water included in the composition for improving melasma is not limited. Usually, it is suitably selected from a range of 50 to 90 wt. %. Preferably, it is selected from a range of 60 to 80 wt. %.

Oils usable in the invention are not limited. Specific examples include peanut oil, sesame oil, soybean oil, safflower oil, avocado oil, sunflower oil, corn oil, rapeseed oil, cottonseed oil, castor oil, camellia oil, coconut oil, olive oil, poppy oil, cacao oil, jojoba oil, and like vegetable oils; beef tallow, lard, lanolin, and like animal oils and fats; petrolatum, liquid paraffin, squalane, α-olefin oligomers, and like hydrocarbon liquid oils; isopropyl myristate, isopropyl isostearate, myristyl myristate, cetyl palmitate, cetyl isooctate, isocetyl myristate, n-butyl myristate, octyldodecyl myristate, isopropyl linolenate, propyl ricinoleate, isopropyl ricinoleate, isobutyl ricinoleate, heptyl ricinoleate, diethyl sebacate, diisopropyl adipate, and like higher fatty acid esters; white beeswax, whale wax, Japan wax, and like waxes; cetyl alcohol, stearyl alcohol, behenyl alcohol, batyl alcohol, chimyl alcohol, and like higher aliphatic alcohols; waxes; stearic acid, oleic acid, palmitic acid, and like higher fatty acids; mono-, di-, or triglyceride mixtures of $C_{12-18}$ saturated or unsaturated fatty acids; methyl polysiloxane, dimethyl polysiloxane, methylphenyl polysiloxane, methyl hydrogen polysiloxane, and like linear silicones; decamethylcyclopentasiloxane, octamethylcyclotetrasiloxane, methylcyclosiloxane, and like cyclic silicones; crosslinked methyl polysiloxane, crosslinked methylphenyl polysiloxane, and like crosslinked silicones; and, for example, silicone oils such as silicones modified by polyoxyethylene, polyoxypropylene or the like; in addition to others. Preferable are hydrocarbon liquid oils such as vaseline, liquid paraffin, squalane, α-olefin oligomer, and the like. Such oils may be used singly or in combination. When oils are solid, it is preferable to liquefy them by means of an auxiliary resolvent before use. It is preferable to use the oil in a proportion of 0.3 to 20 wt. % based on the total amount of the composition for improving melasma, more preferably in a proportion of 0.5 to 15 wt. %.

Although the preparation method for the composition for improving melasma in the form of an O/W emulsion composition is not limited, it is preferable to prepare it according to the method described below:

(1) The polyglyceryl fatty acid ester and the alkanoyl lactic acid or a salt thereof are mixed with the oil and preferably with a polyhydric alcohol. The mixture is stirred while being heated. After the mixture is uniformly dissolved, it is cooled to give a nonaqueous emulsion.

(2) The nonaqueous emulsion thus obtained is blended with an aqueous solution (aqueous composition) that is separately prepared and contains the purine nucleic acid-related substance, water and the acrylic acid-alkyl methacrylate copolymer. The composition for improving melasma in the form of an O/W emulsion is then prepared according to a conventional method.

It is preferable to use the polyhydric alcohol in Process (1) for preparing the nonaqueous emulsion in order to further improve the development of the emulsifying ability of the polyglyceryl fatty acid ester, the alkanoyl lactic acid, etc.

Polyhydric alcohols usable herein are not limited. Specific examples include polyglycerols having a polymerization degree of 2 to 10 (for example, diglycerol, triglycerol, tetraglycerol, etc.), ethylene glycol, diethylene glycol, polyethylene glycol, 1,3-butylene glycol, propylene glycol, dipropylene glycol, isoprene glycol, pentadiol, sorbitol, maltitol, fructose, and the like. The use of glycerol is preferable. Such polyhydric alcohols may be used singly or in combination.

When used, the polyhydric alcohol is used in a proportion of 0.05 to 15 wt. % based on the total amount of the composition for improving melasma, preferably in a proportion of 3 to 10 wt. %.

In Process (2), which is for emulsification, a lower alcohol can be incorporated in addition to the electrolyte, water, and the acrylic acid-alkyl methacrylate copolymer in the aqueous solution (aqueous composition) that is to be blended with the nonaqueous emulsion. This enhances the percutaneous absorption of the purine nucleic acid-related substance. Lower alcohols usable in the invention are not limited, but are usually suitably selected from alcohols having 1 to 6 carbons. Preferable examples are ethanol, propanol, isopropanol, and like $C_{1-4}$ alcohols. Such lower alcohols may be used singly or in combination. The use of ethanol is preferable. When used, the lower alcohol is used in a proportion of 0.5 to 15 wt. % based on the total amount of the composition for improving melasma, preferably in a proportion of 3 to 10 wt. %.

Moreover, a polyhydric alcohol can be used in the aqueous solution described above (aqueous composition). The use thereby makes it possible to control the moisturizing ability and sensory characteristics of the composition for improving melasma to the desired degree. Polyhydric alcohols usable in the aqueous solution include those identified above. When a polyhydric alcohol is used in the preparation of a nonaqueous emulsion, it is preferable to use polyhydric alcohols that are identical or highly compatible with those for the aqueous solution.

Examples of the method for emulsifying the mixture of the nonaqueous emulsion and the aqueous solution (aqueous composition) include stirring the mixture under atmospheric pressure or high pressure using a homomixer. The particles of the resulting emulsion can be further refined by a homogenizer as required.

The proportion of the nonaqueous emulsion to the aqueous solution (aqueous composition) is not limited. It is usually desirable to control the proportion of the nonaqueous emulsion to 1 to 40 wt. %, preferably 1 to 30 wt. %, based on the total amount of the composition for improving melasma, to thereby give a composition for improving melasma in the form of a more stable O/W emulsion composition.

The viscosity of the composition for improving melasma of the invention in the form of the O/W emulsion composition is not limited. It is usually desirable to prepare the O/W emulsion composition to have a viscosity of 30000 cps or less, preferably 500 to 20000 cps, at a temperature of 20° C. (Viscometer: B-type viscometer, Rotor: No. 1 to 4, Rotation rate: 6, 12, 30, or 60 rpm).

The above-described composition for improving melasma of the invention exerts the effect of improving melasma, when applied in the form of the externally-applied compositions to a melasma lesion, due to the effect of the purine nucleic acid-related substances included in the composition. Accordingly, the composition for improving melasma of the present invention can be formulated into externally-applied compositions such as an externally-applied medical or quasi-medical drug, a cosmetic, etc. The composition for improving melasma of the invention is not limited in purpose; specific purposes include externally-applied medical drugs, externally-applied quasi-medical drugs; makeup cosmetics such as foundations, rouges, mascaras, eye shadows, eyeliners, face powders, lip sticks, etc; basic skin care products such as emulsions, creams, lotions, oils and packs; washes such as facial washes, cleansing creams and body washes; cleaning agents; cleaners; bath agents, etc.

The composition for improving melasma of the invention usually has a pH in the range of 2 to 8. In view of low irritation to the skin and mucosa and pleasant skin feeling upon use, it is preferable to have a pH in the range of 2 to 7, more preferably 3 to 7, and further more preferably a weakly acidic pH of 5 to neutral pH of 7.

The composition for improving melasma of the invention can exert the effect of improving melasma by being attached, sprayed or directly applied to a melasma lesion of the skin. The amount and frequency of application of the composition for improving melasma may be determined according to the types and concentrations of the purine nucleic acid-related substances used, the age of the user, the gender, the condition of the affected part of the skin, the application form, the effect intended, etc. The composition for improving melasma of the invention may be applied to the melasma lesion in a suitable amount once or several times per day.

As described above, purine nucleic acid-related substances have the effect of improving melasma. Therefore, the present invention provides the use of purine nucleic acid-related substances for the production of a composition for improving melasma.

(2) A Composition for Reducing Skin Dullness

The composition for reducing skin dullness of the present invention comprises a purine nucleic acid-related substance, and a pharmaceutically or cosmetically acceptable carrier.

The composition for reducing skin dullness of the invention can contain purine nucleic acid-related substances or pharmaceutically or cosmetically acceptable carriers that are the same as those used in the above composition for improving melasma.

The proportion for incorporating the purine nucleic acid-related substances into the composition for reducing skin dullness, the wide variety of additives or medicinal properties that can be added to the composition, the form of the composition, and the pH thereof are the same as those in the above-described composition for improving melasma.

In particular, it is preferable to formulate the composition for reducing skin dullness into emulsion compositions such as emulsions, creams, or the like by blending and emulsifying a polyglyceryl fatty acid ester, alkanoyl lactic acid or a salt thereof, an acrylic acid-alkyl methacrylate copolymer, water, and an oil with a purine nucleic acid-related substance. More preferably, the composition is prepared by further blending a polyhydric alcohol and/or a lower alcohol. The O/W emulsion composition for reducing skin dullness thus obtained is in a stable emulsified state without separation and oil floating, and can effectively exhibit the effect of reducing skin dullness. The type of polyglyceryl fatty acid esters, alkanoyl lactic acids or salts thereof, acrylic acid-alkyl methacrylate copolymers, water, oils, polyhydric alcohols and lower alcohols that are usable in the O/W emulsion composition; amounts thereof; preparation methods thereof; and viscosities thereof, are the same as those in the composition for improving melasma in the form of the O/W emulsion composition.

The composition for reducing skin dullness of the invention can exert the effect of reducing skin dullness by being attached, sprayed, or directly applied to the dullness region of the skin. The amounts and frequencies of application of the composition for improving melasma may be determined according to the type of purine nucleic acid-related substances used, the concentrations thereof, the age of the user, the gender, the condition of the affected part of the skin, the application form, the effect intended, etc. The composition for reducing skin dullness of the invention may be applied to the dullness region of the skin in a suitable amount once or several times per day.

As described above, purine nucleic acid-related substances have the effect of reducing skin dullness. Therefore, the present invention provides the use of purine nucleic acid-related substances for production of a composition for reducing skin dullness.

(3) A Method for Improving Melasma

As described above, the purine nucleic acid-related substances can effectively improve melasma. Thus, the present invention provides a method for improving melasma using a purine nucleic acid-related substance.

The method for improving melasma of the present invention can be carried out by applying a purine nucleic acid-related substance as such, or a composition comprising the substance to a melasma lesion.

Purine nucleic acid-related substances usable in the method of the invention are the same as used in the above composition for improving melasma.

In the method of the invention, the manner of applying the purine nucleic acid-related substance to the melasma lesion is not limited insofar as the purine nucleic acid-related substance is brought into contact with the melasma legion. For example, the purine nucleic acid-related substance alone, or a composition comprising the substance as an active ingredient and pharmaceutically or cosmetically acceptable bases, carriers, additives, or medicinal agents can be applied to the melasma lesion. More specifically, the substance or the composition comprising it is spread or sprayed onto the target skin portion, or attached to the skin in the form of a patch.

A method of applying the composition for improving melasma to a melasma lesion can be mentioned as a preferable embodiment of the present invention.

The amounts and frequencies of application of the purine nucleic acid-related substance to the lesion may be determined according to the type of purine nucleic acid-related substances used, the age of the user, the gender, the condition of melasma, the application form, the effect intended, etc. The purine nucleic acid-related substance can be applied to the melasma lesion of the skin in a suitable amount once or several times per day.

As described above, by the use of the purine nucleic acid-related substances, a melasma can be effectively improved. Therefore, the present invention also provides the use of purine nucleic acid-related substances for improving melasma.

(4) A Method for Reducing Skin Dullness

As described above, the purine nucleic acid-related substances can effectively reduce skin dullness. Thus, the present invention provides a method for reducing skin dullness using a purine nucleic acid-related substance.

The method for reducing skin dullness of the present invention can be carried out by applying a purine nucleic acid-related substance as such, or a composition comprising the substance to the dullness region of the skin.

Purine nucleic acid-related substances usable in the method of the invention are the same as used in the above composition for reducing skin dullness.

In the method of the invention, the manner of applying the purine nucleic acid-related substance to the dullness region of the skin is not limited insofar as the purine nucleic acid-related substance is brought into contact with the target part. For example, the purine nucleic acid-related substance alone, or a composition comprising the substance as an active ingredient and pharmaceutically or cosmetically acceptable carriers, additives, or medicinal agents can be applied to the dullness region of the skin. More specifically, the substance or the composition comprising it is spread or sprayed onto the target skin portion, or attached to the skin in the form of a patch.

A method of applying the composition for reducing skin dullness to a dullness region of the skin can be mentioned as a preferable embodiment of the present invention.

The amounts and frequencies of application of the purine nucleic acid-related substances to the dullness region of the skin may be determined according to the type of purine nucleic acid-related substances used, the age of the user, the gender, the intended use, the condition of the dullness region, the application form, etc. The purine nucleic acid-related substance can be applied to the dullness region of the skin in a suitable amount once or several times per day.

As described above, by the use of the purine nucleic acid-related substance, the skin dullness can be effectively reduced. Therefore, the present invention also provides the use of the purine nucleic acid-related substance for reducing skin dullness.

EXAMPLES

The present invention is described in more detail with reference to the following examples, although the present invention is not limited to these examples.

Example 1

Emulsions

|  | (wt. %) |
|---|---|
| Disodium adenosine 5'-monophosphate | 3.0 |
| Sodium isostearoyl lactate | 0.2 |
| Acrylic acid-alkyl methacrylate copolymer | 0.4 |
| Light liquid paraffin | 5.0 |
| Glycerol | 6.0 |
| Ethanol | 5.0 |
| Antiseptic | Suitable amount |
| Decaglycerol monoisostearate | 1.5 |
| Decaglycerol monomyristate | 0.3 |
| pH Adjuster | (pH 6.5) |
| Pure water | Balance |
|  | 100.0 wt. % |

An emulsion was produced by the method described below according to the above formulation. The decaglycerol monoisostearate, decaglycerol monomyristate, sodium isostearoyl lactate, glycerol, and light liquid-paraffin were blended, dissolved while being heated, and cooled, to prepare a uniform nonaqueous emulsion. Mixed therewith was an aqueous composition (aqueous solution) that was separately prepared by dissolving in distilled water (pure water) the disodium adenosine 5'-monophosphate, acrylic acid-alkyl methacrylate copolymer, ethanol, antiseptic agent and pH adjuster. The mixture was stirred by a homomixer to become an emulsion in an O/W-emulsified state.

Test Example 1

Melasma Improving Test

The following tests were conducted to evaluate the effect of improving melasma of a purine nucleic acid-related substance.

<Test Method>

A suitable amount (an amount that can be uniformly applied to an entire face: about five drops) of the emulsion prepared according to the formulation of Example 1 was applied over the entire face of 27 patients with melasma, twice per day, after washing of the face, and this was continued for 16 weeks (except for one person who stopped by 12 weeks). Before initiation of the application, 4, 8, 12, and 16 weeks after initiation of the application, a dermatologist made an overall evaluation of the color intensity and the range of melasma, and classified the condition of the melasma of each patient into five grades, "no melasma", "slight", "mild", "moderate", and "severe", according to the criteria of the following table 1.

TABLE 1

| | | Range | | | |
|---|---|---|---|---|---|
| Symptom | | None | Ultra-narrow | Narrow | Moderate | Wide |
| Color intensity | None | None | None | None | None | None |
| | Slightly weak | None | None | Slight | Slight | Mild | Moderate |
| | Weak | None | Slight | Mild | Moderate | Moderate |
| | Moderate | None | Slight | Moderate | Severe | Severe |
| | Strong | None | Moderate | Moderate | Severe | Severe |

The dermatologist-diagnosed melasma grades of the patients were compared before and after initiation of the application to evaluate the degree of melasma improving according to the following criteria.

Evaluation Criteria of the Degree of Melasma Improvement

| Cured | All symptoms disappeared |
|---|---|
| Improvement | Improvement of two grades or better by the criteria of Table 1 achieved |
| Slight improvement | Improvement was observed: less than two grades by the criteria of Table 1 |
| No change or aggravation | No improvement |

Test Results

The obtained results are shown in Table 2. Table 2 shows the number of patients that met each of the above evaluation criteria of the melasma improving grade, the proportion of "slight improvement" or better (the proportion (%) of patients that showed "slight improvement" or better), and the 95% confidence interval of the percentage of patients with "slight improvement" or better, 4, 8, 12, and 16 weeks after initiation of the application.

TABLE 2

| | Degree of melasma improvement (the number of the patients) | | | | Proportion of slight improvement or better (%) | 95% confidence interval |
|---|---|---|---|---|---|---|
| | Cured | Improvement | Slight improvement | No change or aggravation | | |
| 4 weeks after initiation of the external application | 0 | 0 | 5 | 22 | 18.5 | 6.3-38.1 |
| 8 weeks after initiation of the external application | 0 | 5 | 10 | 12 | 55.6 | 35.3-74.5 |
| 12 weeks after initiation of the external application | 0 | 10 | 10 | 7 | 74.1 | 53.7-88.9 |
| 16 weeks after initiation of the external application | 0 | 10 | 14 | 2 | 92.3 | 74.9-99.1 |

As is evident from Table 2, the remarkable effect of improving melasma was exhibited by the use of emulsions comprising AMP2Na. More specifically, 12 weeks after initiation of the external application, 74.1% of the patients, and 16 weeks after initiation of the application, 92.3% of the patients showed improvement of melasma, and it was found that the effect of improving melasma was statistically significant.

The above test results showed that the purine nucleic acid-related substance, when applied to the melasma lesion, exhibited an excellent melasma improving effect, and thus it was found that the substance is useful for improving melasma.

Test Example 2

Test for Reducing Skin Dullness

The following tests were conducted to evaluate the skin dullness reduction effect of a purine nucleic acid-related substance.

Test Method

A suitable amount (an amount that can be uniformly applied to the entire face: about five drops) of the emulsion prepared according to the formulation of Example 1 was applied over the entire face of 27 females with skin dullness, twice per day, after washing of the face, and this was continued for 16 weeks. Before initiation of the application, and 4, 8, 12, and 16 weeks after initiation of the application, the skin color tone of the subjects was measured using a color difference meter (OFC-300A, Nippon Denshoku Industries Co., Ltd.). The measurement value was obtained by measuring a $L^*$ value indicating lightness of the skin, an $a^*$ value indicating redness of the skin, and a $b^*$ value indicating yellowness of the skin of the evaluation target region of each patient 11 times, and calculating the mean of 7 measurement values of 11 values, excluding the 2 maximum and 2 minimum values.
Test Results
The obtained results are shown in FIG. 1. FIG. 1 shows the mean average of the variation, $\Delta L^*$ of the $L^*$ value indicating skin lightness, the mean average of the variation, $\Delta a^*$ of the value $a^*$ indicating redness, and the variation, $\Delta E^*ab$ indicating color difference of the skin, $(E^*ab)$, 4, 8, 12, and 16 weeks after initiation of the application as compared to the $L^*$ value, the $a^*$ value and the $b^*$ value of the subjects before application of the composition. The $\Delta E^*ab$ value was calculated by formula 1.

$$\Delta E^*ab=[(\Delta L^*)^2+(\Delta a^*)^2+(\Delta b^*)^2]^{1/2}$$ Formula 1

By the application of the emulsions comprising AMP2Na to the skin, the $L^*$ value of the skin (skin lightness) was significantly increased 4 weeks after initiation of the application, while the $b^*$ value indicating yellowness was significantly reduced 4 weeks after initiation of the application. The $a^*$ value indicating redness started to increase about 8 weeks after initiation of the application, and the increase was significant 12 weeks after the initiation. The trend in the change of the $a^*$ value indicating redness showed that the change in the skin redness was not caused by the transient improvement in blood flow. It is known that the $\Delta E^*ab$ value as an index for showing a change in color difference represents a total change in the skin with respect to lightness, redness, and yellowness, and in general the change in the skin can be subjectively and objectively observed when the $\Delta$ value generally reaches 2 or higher. Since the $\Delta E^*ab$ value 4 weeks after initiation of the application was already above 2, it was found that the skin color tone had already notably changed.

The above test results showed that the purine nucleic acid-related substance exhibits an excellent skin dullness reduction effect when applied to the dullness region of the skin, and thus it was found that the substance is useful for reducing the skin dullness.

Test Example 3

An Emulsion Stability Test for the Composition for Improving Melasma or Reducing Skin Dullness in an O/W Emulsified State The following tests were conducted to evaluate the emulsion stability of a composition for improving melasma or reducing skin dullness in an O/W emulsified state.
Test Method
For evaluation of the emulsion stability test for a composition for improving melasma or reducing skin dullness in an O/W emulsified state, a composition for improving melasma or reducing skin dullness was prepared according to the formulation shown in Table 3. First, a polyglyceryl fatty acid ester, an alkanoyl lactate, an oil, and a polyhydric alcohol were blended, dissolved while being heated, and cooled, to prepare a uniform nonaqueous emulsion. Mixed therewith was an aqueous composition (aqueous solution) that was separately prepared by dissolving in distilled water (pure water) an electrolyte, an acrylic acid-alkyl methacrylate copolymer, a polyhydric alcohol, a lower alcohol, a pH adjuster, and an antiseptic. The mixture was stirred by a homomixer to give a composition for improving melasma or reducing skin dullness in an O/W emulsified state (Examples 2 to 5). For comparison, a composition for improving melasma comprising no alkanoyl lactate (Comparative Example 1), and a composition for reducing skin dullness comprising no acrylic acid-alkyl methacrylate copolymer (Comparative Example 2) were prepared in the same manner as in Examples 2 to 5 (Table 4 shows the ingredients for these emulsion compositions).

The ten compositions for improving melasma or reducing skin dullness (Examples 2 to 5 and Comparative Examples 1 and 2) thus prepared were each placed in two transparent glass bottles. One bottle was left to stand at a temperature of 60° C. for 2 weeks, and the other bottle was subjected to a 14-cycle test at temperatures ranging from −5° C. to 40° C. (1 cycle: 24 hours). The appearance (separation, oil floating, presence/absence of gel formation) of each emulsion composition after the test was visually observed and evaluated according to the following criteria.
<Evaluation Criteria>
A: Neither separation, oil floating, nor gel formation was observed.
B: Separation, oil floating, or gel formation was observed.

TABLE 3

|   |   | Ex. 2 | Ex. 3 | Ex. 4 | Ex. 5 |
|---|---|---|---|---|---|
| 1 | Decaglycerol monoisostearate | — | 1.6 | 0.16 | 4.8 |
| 2 | Decaglycerol diisostearate | 1.2 | — | — | — |
| 3 | Decaglycerol monostearate | — | — | 0.02 | 0.5 |
| 4 | Decaglycerol monomyristate | 0.6 | 0.2 | — | — |
| 5 | Sodium stearoyl lactate | — | — | 0.02 | — |
| 6 | Sodium isostearoyl lactate | 0.2 | 0.2 | — | 0.5 |
| 7 | Squalane | 5.0 | 8.0 | — | 15.0 |
| 8 | α-Olefin oligomer | — | — | 5.0 | — |
| 9 | Purified glycerol | 6.0 | 6.0 | 2.0 | 9.0 |
| 10 | Dipropylene glycol | — | — | 5.0 | — |
| 11 | Disodium adenosine monophosphate | 1.5 | 1.5 | 3.0 | 6.0 |
| 12 | Acrylic acid-alkyl methacrylate copolymer | 0.4 | 0.5 | 0.5 | 0.5 |
| 13 | Ethanol | 5.0 | 5.0 | 3.0 | 5.0 |
| 14 | pH Adjuster | Suitable amount | Suitable amount | Suitable amount | Suitable amount |
| 15 | Antiseptic | Suitable amount | Suitable amount | Suitable amount | Suitable amount |
| 16 | Pure water | Remainder | Remainder | Remainder | Remainder |
|   | Viscosity (cps) 20° C. | 4200 | 17000 | 1400 | 1100 |
|   | Long-term stability (60° C.: 2 weeks) | A | A | A | A |
|   | Long-term stability (−5 to 40° C. cycles: 2 weeks) | A | A | A | A |

TABLE 4

|   |   | Comp Ex. 1 | Comp Ex. 2 |
|---|---|---|---|
| 1 | Decaglycerol monoisostearate | 2.0 | — |
| 2 | Decaglycerol diisostearate | — | 1.2 |
| 3 | Decaglycerol monomyristate | — | 0.6 |
| 4 | Sodium isostearoyl lactate | — | 0.2 |
| 5 | Squalane | 5.0 | — |
| 6 | α-Olefin oligomer | — | 5.0 |
| 7 | Purified glycerol | 6.0 | 8.0 |
| 8 | Carboxyvinyl polymer | — | 0.6 |
| 9 | Disodium adenosine monophosphate | 3.0 | 3.0 |
| 10 | Acrylic acid-alkyl methacrylate copolymer | 0.5 | — |
| 11 | Ethanol | 3.0 | 5.0 |
| 12 | pH Adjuster | Suitable amount | Suitable amount |
| 13 | Antiseptic | Suitable amount | Suitable amount |

TABLE 4-continued

| | Comp Ex. 1 | Comp Ex. 2 |
|---|---|---|
| 14 Pure water | Remainder | Remainder |
| Viscosity (cps) 20° C. | 2,000 | 1,200 |
| Long-term stability (60° C.: 2 weeks) | A | B |
| Long-term stability (−5 to 40° C. cycles: 2 weeks) | B | A |

Test Results

Tables 3 and 4 show the results of the emulsion stability test for the compositions for improving melasma of Examples 2 to 5 and Comparative Examples 1 and 2.

As can be seen from the tables 3 and 4, the compositions for improving melasma or reducing skin dullness in an O/W emulsified state of Examples 2 to 5 inhibit water/oil phase separation, oil floating and gel formation and stably maintains their emulsified state under conditions in which the emulsion compositions are likely to be affected by long-term storage and temperature change, even when they contain a relatively large amount of AMP2Na. In contrast, as the comparative examples show, the emulsion composition in an O/W emulsified state comprising no acrylic acid-alkyl methacrylate copolymer (Comparative Example 2) lacked long-term emulsion stability, and the emulsion composition comprising no alkanoyl lactate (Comparative Example 1) gelated with temperature change, thus failing to maintain a stable emulsified state.

As is clear from the above, when formulated into an O/W emulsion composition as previously described, the composition for improving melasma or reducing the skin dullness can be provided in the form of emulsions or creams in a stable manner.

INDUSTRIAL APPLICABILITY

The composition for improving melasma of the invention exhibits an excellent melasma improving effect due to the action of the purine nucleic acid-related substance when applied to a melasma lesion.

The composition for reducing skin dullness of the invention exhibits an excellent effect of reducing the skin dullness due to the action of the purine nucleic acid-related substance when applied to a dullness region of the skin.

The purine nucleic acid-related substance included as an active ingredient in the composition for improving melasma or for reducing skin dullness is highly safe to the human body since such a substance is intrinsically present in the living body. Thus, the substance can be included in cosmetics in addition to externally-applied medical or quasi-medical drugs. Therefore, the present invention provides a means for improving melasma or skin dullness which can be carried out by the daily use of a cosmetic comprising the substance, and thus is easy for patients to use.

Further, the composition for improving melasma or reducing skin dullness in an O/W emulsified state of the invention has a favorable emulsion stability in addition to an excellent effect for improving melasma or reducing the skin dullness, and thus is useful as an externally-applied agent for the skin in the form of a cream or emulsion.

The method for improving melasma of the invention makes it possible to effectively improve melasma.

The method for reducing skin dullness of the invention makes it possible to effectively reduce the skin dullness.

The invention claimed is:

1. A method for improving melasma, comprising applying, to a melasma lesion, an externally-applied medical or cosmetic composition comprising an adenosine monophosphate or a salt thereof, a polyglyceryl fatty acid ester, an alkanoyl lactic acid or a salt thereof, an acrylic acid-alkyl methacrylate copolymer, water, an oil, a polyhydric alcohol, and a lower alcohol having 1 to 6 carbons; wherein the proportion of the adenosine monophosphate or a salt thereof is 1 to 10 weight percent based on the total amount of the composition; wherein the adenosine monophosphate is at least one member selected from the group consisting of adenosine 2'-monophosphate, adenosine 3'-monophosphate, and adenosine 5'-monophosphate; and wherein the composition is formulated into an oil-in-water (O/W)-type emulsion.

2. The method for improving melasma according to claim 1, wherein the polyglyceryl fatty acid ester and the alkanoyl lactic acid or a salt of the alkanoyl lactic acid are present in the composition in a weight ratio of 95:5 to 60:40.

3. The method for improving melasma according to claim 2, wherein the polyglyceryl fatty acid ester is an ester of a $C_{12-36}$ fatty acid and a polyglycerol having a polymerization degree of 6 or more, the alkanoyl lactic acid comprises an alkanoyl group having 8 or more carbons, the acrylic acid-alkyl methacrylate copolymer comprises a $C_{5-40}$ alkyl group, and the oil is a hydrocarbon liquid oil.

4. The method for improving melasma according to claim 2, wherein the composition comprises the polyglyceryl fatty acid ester in a proportion of 0.05 to 6 wt. %, the alkanoyl lactic acid or a salt thereof in a proportion of 0.01 to 1 wt. %, the acrylic acid-alkyl methacrylate copolymer in a proportion of 0.01 to 0.8 wt. %, the oil in a proportion of 0.3 to 20 wt. %, the polyhydric alcohol in a proportion of 0.05 to 15 wt. %, and water in a proportion of 50 to 90 wt. %, based on the total amount of the composition.

5. A method for reducing skin dullness, comprising applying, to a dullness region of the skin, an externally-applied medical or cosmetic composition comprising an adenosine monophosphate or a salt thereof, a polyglyceryl fatty acid ester, an alkanoyl lactic acid or a salt thereof, an acrylic acid-alkyl methacrylate copolymer, water, an oil, a polyhydric alcohol, and a lower alcohol having 1 to 6 carbons; wherein the proportion of the adenosine monophosphate or a salt thereof is 1 to 10 weight percent based on the total amount of the composition; wherein the adenosine monophosphate is at least one member selected from the group consisting of adenosine 2'-monophosphate, adenosine 3'-monophosphate, and adenosine 5'-monophosphate; and wherein the composition is formulated into an O/W-type emulsion.

6. The method for reducing skin dullness according to claim 5, wherein the polyglyceryl fatty acid ester and the alkanoyl lactic acid or a salt of the alkanoyl lactic acid are present in the composition in a weight ratio of 95:5 to 60:40.

7. The method for reducing skin dullness according to claim 6, wherein the polyglyceryl fatty acid ester is an ester of a $C_{12-36}$ fatty acid and a polyglycerol having a polymerization degree of 6 or more, the alkanoyl lactic acid comprises an alkanoyl group having 8 or more carbons, the acrylic acid-alkyl methacrylate copolymer comprises a $C_{5-40}$ alkyl group, and the oil is a hydrocarbon liquid oil.

8. The method for reducing skin dullness according to claim 6, wherein the composition comprises the polyglyceryl fatty acid ester in a proportion of 0.05 to 6 wt. %, the alkanoyl lactic acid or a salt thereof in a proportion of 0.01 to 1 wt. %, the acrylic acid-alkyl methacrylate copolymer in a proportion of 0.01 to 0.8 wt. %, the oil in a proportion of 0.3 to 20 wt. %, the polyhydric alcohol in a proportion of 0.05 to 15 wt. %, and water in a proportion of 50 to 90 wt. %, based on the total amount of the composition.

* * * * *